United States Patent
Shaked et al.

(10) Patent No.: US 11,155,614 B2
(45) Date of Patent: Oct. 26, 2021

(54) CANCER TREATMENT BY BLOCKING HOST-INDUCED IL-1 IN COMBINATION WITH RADIOTHERAPY

(71) Applicant: OncoHost Ltd., Binyamina (IL)

(72) Inventors: Yuval Shaked, Binyamina (IL); Eyal Jacob, Haifa (IL); Ella Fremder, Haifa (IL)

(73) Assignee: OncoHost Ltd., Binyamina (IL)

( * ) Notice: Subject to any disclaimer, the term of this patent is extended or adjusted under 35 U.S.C. 154(b) by 0 days.

(21) Appl. No.: 16/425,595

(22) Filed: May 29, 2019

(65) Prior Publication Data

US 2019/0367603 A1 Dec. 5, 2019

Related U.S. Application Data

(60) Provisional application No. 62/757,284, filed on Nov. 8, 2018, provisional application No. 62/677,267, filed on May 29, 2018.

(51) Int. Cl.
| | |
|---|---|
| *G01N 33/53* | (2006.01) |
| *A61K 39/00* | (2006.01) |
| *A61K 38/20* | (2006.01) |
| *C07K 16/24* | (2006.01) |
| *A61P 35/00* | (2006.01) |
| *A61K 38/00* | (2006.01) |
| *A61N 5/10* | (2006.01) |

(52) U.S. Cl.
CPC .......... *C07K 16/245* (2013.01); *A61K 38/005* (2013.01); *A61K 38/2006* (2013.01); *A61K 39/001119* (2018.08); *A61N 5/10* (2013.01); *A61P 35/00* (2018.01); *G01N 33/53* (2013.01); *A61K 2039/545* (2013.01)

(58) Field of Classification Search
CPC ..................................................... A61K 39/00
See application file for complete search history.

(56) References Cited

U.S. PATENT DOCUMENTS

2017/0260285 A1* 9/2017 Burnett .................. A61K 45/06

FOREIGN PATENT DOCUMENTS

| WO | 2018225062 A1 | 12/2018 |
| WO | 2018225063 A1 | 12/2018 |

OTHER PUBLICATIONS

Beers and Berkow, The Merck Manual, 17th edition, (1999), pp. 165-177, and pp. 986-995.*
Janko et al Radiation Research, (2012), September, 178(3): 166-172.*
Di Maggio et al. Journal of Inflammation (2015) 12:14.*
York et al., The biobehavioral and neuroimmune impact of low-doseionizing radiation, Brain Behav Immun. 26(2): 218-227. (2012).
WIPO International Search Report for PCT/IL2019/050614, pp. 4, dated Aug. 19, 2019.
Apte, et al; "The involvement of IL-1 in tumorigenesis, tumor invasiveness, metastasis and tumor-host interactions". Cancer Metastasis Rev. 25(3): 387-408 (2006).
Beyar-Katz, et al; "Bortezomib-induced proinflammatory macrophages as a potential factor limiting anti-tumour efficacy". J. Pathol. 239: 262-273 (2016).
Dinarello; "Why not treat human cancer with interleukin-1 blockade?" Cancer Metastasis Rev. 29: 317-329 (2010).
Gingis-Velitski, et al; "Host response to short-term, single-agent chemotherapy induces matrix metalloproteinase-9 expression and accelerates metastasis in mice". Cancer Res. 71(22): 6986-6996 (2011).
Rachman-Tzemah, et al; "Blocking Surgically Induced Lysyl Oxidase Activity Reduces the Risk of Lung Metastases". Cell Rep. 19(4): 774-784 (2017).
Shaked; "Balancing efficacy of and host immune responses to cancer therapy: the yin and yang effects". Nat. Rev. Clin. Oncol. 13(10): 611-26 (2016).
Timaner, et al; "Dequalinium blocks macrophage-induced metastasis following local radiation". Oncotarget 6(29): 27537-27554 (2015).
Timaner, et al; "Analysis of the Stromal Cellular Components of the Solid Tumor Microenvironment Using Flow Cytometry". Curr. Protoc. Cell Biol. 70:19.18.1-19.18.12 (2016).
Voronov, et al; "IL-1 is required for tumor invasiveness and angiogenesis". Proc. Natl. Acad. Sci. U S A 100(5): 2645-2650 (2003).

* cited by examiner

*Primary Examiner* — Prema M Mertz
(74) *Attorney, Agent, or Firm* — The Roy Gross Law Firm, LLC; Roy Gross (57) ABSTRACT

Provided are blocking agents to IL-1α, IL-1β, or IL-1R activity for use in combination with radiotherapy for treating cancer patients in which radiotherapy treatment induces IL-1α, IL-1β or both in their circulation.

19 Claims, 8 Drawing Sheets

CANCER TREATMENT BY BLOCKING HOST-INDUCED IL-1 IN COMBINATION WITH RADIOTHERAPY

CROSS REFERENCE

The present application claims priority and the filing date of U.S. Provisional Application No. 62/757,284, filed Nov. 8, 2018, and U.S. Provisional Application No. 62/677,267, filed May 29, 2018, the entire contents of each and all these applications being hereby incorporated by reference herein in their entirety as if fully disclosed herein.

FIELD OF THE INVENTION

The present invention is in the field of oncology and relates in general to methods for treating cancer and, in particular, to methods combining radiotherapy with the blocking of IL-1α, IL-1β or their receptor IL-1R.

BACKGROUND OF THE INVENTION

Tumors do not exist independently in the host organism. Instead, cancer cells grow in the host organism surrounded by a complex microenvironment composed of stromal cells including fibroblasts, endothelial cells and cells of the immune system. The various components of the microenvironment and the cancer cells interact with each other and affect each other by direct cell-cell contact and secretion of cytokines and other factors.

Many of the local and systemic therapies for cancer can be curative in patients with early stage disease, but they are less frequently successful when used to treat advanced-stage and/or metastatic disease. In addition, tumors often develop resistance to therapy even when an initial tumor response to treatment is observed. Many studies have focused on the contribution of mutations and genetic aberrations in the tumor cells which promote drug resistance and can explain tumor re-growth. Other studies have highlighted the contribution of therapy-induced physiological changes in host tissues and cells that can reduce or even nullify the desired antitumor effects of therapy. These unwanted host effects can promote tumor-cell proliferation (repopulation) and even malignant aggressiveness.

We and others have disclosed that almost any type of anti-cancer treatment modality including radiotherapy, chemotherapy, targeted cancer drugs, immunotherapy and surgery generates a spectrum of systemic effects in the treated cancer patient that may counteract the desired therapeutic effect of the cancer therapy modality. These effects include a rapid induction of circulating cytokines and growth factors accompanied by acute mobilization and tumor homing of various bone-marrow derived cells (Shaked, 2016; Shaked et al., 2008; Gingis-Velitski et al., 2011; Timaner et al., 2015; Beyar-Katz et al., 2016; Rachman-Tzemah et al., 2017). This response to cancer therapy, termed "host response", occurs independently of the tumor, but has the potential to affect tumor fate through various mechanisms.

In our two International Patent Applications filed on Jun. 4, 2018, Nos. PCT/IL2018/050608 (WO 2018/225062) and PCT/IL2018/050609 (WO 2018/225063), titled "Method of Predicting Personalized Response to Cancer Therapy and Kit therefor" and "Method of Predicting Personalized Response to Cancer Treatment with Immune Checkpoint Inhibitors and Kits therefor", respectively, the entire contents of which are hereby incorporated herein by reference, in which the main inventor in the present application is also the main inventor, we have described a method for identifying a plurality of factors/biomarkers generated by the cancer patient in response to a cancer therapy (host response) and determining how a change in the levels of each of two or more of the plurality of factors as compared to a reference level, predicts a favorable or a non-favorable response of the cancer patient to the treatment with said cancer therapy. These molecular factors are cytokines, chemokines, growth factors, enzymes or soluble receptors that may be pro-angiogenic, pro-inflammatory/chemotactic, proliferative, or pro-metastatic factors.

Several circulating pro-inflammatory factors/biomarkers generated by cancer patients in response to cancer therapies such as chemotherapy, radiotherapy, and targeted therapy were identified in the above-mentioned PCT/IL2018/050608. Among these pro-inflammatory factors/biomarkers are IL-1α and IL-1β.

Interleukin-1 (IL-1), the first interleukin to be identified, is a central mediator of innate immunity and inflammation. There are two related but distinct IL-1 genes, IL1A and IL1B, encoding IL-1α and IL-1β, respectively. In most studies, their biological activities are indistinguishable; however, IL-1α and IL-1β have several differences: IL-1β is secreted and circulates systemically, whereas IL-1α is generally associated with the plasma membrane of the producing cell and so acts locally. Secondly, IL-1β is mainly produced by monocytes and macrophages, whereas IL-1α is highly expressed by keratinocytes and endothelial cells. Although IL-1α and IL-1β have these differences, both of them bind to the same receptor complex including IL-1 receptor type 1 (IL-1R1) and IL-1RAcP, and signal through myeloid differentiation primary response protein (MyD88). This signaling can be negatively regulated by IL-1 receptor antagonist, IL-1Ra, which is the natural antagonist of IL-1α and IL-1β. The naturally occurring IL-1 receptor antagonist (IL-1Ra) is structurally similar to IL-1β, but lacks agonist activity. In addition, regulation of IL-1 activity extends to low numbers of surface receptors, circulating soluble receptors and a cell surface "decoy" receptor to down-regulate responses to IL-1β.

IL-1 plays a significant role in the mediation of a number of inflammatory diseases such as rheumatoid arthritis, gout, and others. IL-1 has also been disclosed as involved in tumorigenesis, tumor invasiveness, metastasis and tumor-host interactions (Dinarello, 2010; Apte et al. 2006; Voronov et al., 2003).

SUMMARY OF THE INVENTION

It has now been found, in accordance with the present invention, that in cancer patients that generate IL-1α or IL-1β, or both, in response to treatment with radiotherapy (herein "host-induced IL-1α or IL-1β"), blocking the activity, particularly the pro-tumorigenic activity, of the host-induced IL-1α or IL-1β, or blocking the IL-1 receptor that is common to both interleukins, can improve the therapeutic outcome of the treatment of the cancer patient with the radiotherapy in combination with said blocking agent.

In one aspect, the present invention relates to a blocking agent to IL-1α, IL-1β or to their receptor IL-1R, selected from an anti-IL-1α, anti-IL-1β and anti-IL-1R, for use in the treatment of a cancer patient, comprising administering said blocking agent to the cancer patient in combination with radiotherapy, wherein the radiotherapy induces IL-1α, IL-1β or both in the circulation of said cancer patient in response to treatment with the radiotherapy, and determining that the fold-change of each of the induced IL-1α, IL-1β or both in the cancer patient is at least 1.5-fold, this fold-change value being considered significant and predictive of a non-favorable response of the cancer patient to the treatment with said radiotherapy, wherein the fold change is established by comparing: (i) the level of IL-1α, IL-1β or both in a biological sample selected from blood plasma, whole blood, blood serum or peripheral blood mononuclear cells, preferably blood plasma, obtained from the cancer patient after a session of treatment with said radiotherapy, with (ii) a reference level obtained from a biological sample selected from blood plasma, whole blood, blood serum or peripheral blood mononuclear cells, preferably blood plasma, obtained from the cancer patient before said session of treatment with the radiotherapy.

In another aspect, the present invention relates to a method of treating a cancer patient with a blocking agent to IL-1α, IL-1β or to their receptor IL-1R, selected from an anti-IL-1α, anti-IL-1β and anti-IL-1R, in combination with radiotherapy, the method comprising the steps of:

(i) performing an assay on a biological sample selected from blood plasma, whole blood, blood serum or peripheral blood mononuclear cells, preferably blood plasma, obtained from the cancer patient at a time period of about 20 to 24 hours or more after a session of treatment with radiotherapy, to determine the level of IL-1α, IL-1β, or both, in the circulation of said cancer patient in response to treatment with said radiotherapy;

(ii) obtaining a reference level for each of IL-1α, IL-1β, or both, of step (i) in a biological sample selected from blood plasma, whole blood, blood serum or peripheral blood mononuclear cells, preferably blood plasma, obtained from the cancer patient before said session of treatment with the radiotherapy;

(iii) establishing the fold-change of IL-1α, IL-1β, or both, by comparing the level of the IL-1α, IL-1β, or both, of step (i) with the reference level of IL-1α, IL-1β, or both, of step (ii);

(iv) determining that the cancer patient has a non-favorable response to the treatment with said radiotherapy if the fold-change established in step (iii) is at least 1.5, this fold-change value indicating upregulation of induced IL-1α, IL-1β, or both, and being considered significant and predictive of a non-favorable response of the cancer patient to the treatment with said radiotherapy; and (v) treating the cancer patient showing a fold change of at least 1.5 with radiotherapy in combination with a blocking agent to IL-1α, IL-1β, or to their receptor IL-1R activity.

BRIEF DESCRIPTION OF THE FIGURES

FIG. 1B shows the fold-change for IL-1β obtained by calculating the ratio of treatment:reference/baseline IL-1β levels.

FIGS. 2A-2B show inhibition of primary tumor growth by blocking of host-derived IL-1β following radiation. BALB/c mice were orthotopically injected with EMT6 murine breast carcinoma cells in the mammary fat pad. When tumors reached a size of 150-250 mm³, mice were either exposed to a single dose of 2 Gy radiation (FIG. 2A) or to a total of four doses (single dose of 2 Gy radiation twice a week, FIG. 2B). In addition, mice were treated with anakinra (ANK) for 4 sequential days, starting one day before the radiation, or a combination of radiation and anakinra. Control mice were injected with vehicle control. Tumor volume was monitored regularly. Shown are mean values (n=6 mice per group)±SD.

FIGS. 4A-4B show a flow cytometry analysis of tumor-infiltrating immune cells. BALB/c mice were orthotopically injected with EMT6 murine breast carcinoma cells in the mammary fat pad. When tumors reached a size of 150-250 mm³, mice were either exposed to a single dose of local 2Gy radiation and treated with anakinra (ANK) for 4 sequential days, starting two days before the radiation, or with a combination of radiation and anakinra. Control mice were injected with vehicle control. At the end of the experiment (when tumors reached a size of ~1000 mm³), mice were sacrificed, and tumors were removed and prepared as a single cell suspension. Cells were immunostained for biomarkers characterizing different immune cell populations. FIG. 4A shows the percentage of CD8+ T cell lymphocytes and FIG. 4B shows the percentage of MDSCs. Shown are mean values (n=6 mice per group)±SD, *p<0.05.

FIGS. 5A-5C show the increase in IL-1α concentration in response to radiotherapy in non-tumor bearing mice compared to control. Six weeks old naïve female BALB/c mice (n=5) were exposed to a single dose of 2Gy radiation in the abdominal cavity (treatment group) or were not treated (control group). After 24 hours, mice were sacrificed, and blood was collected into EDTA-coated tubes by cardiac puncture. Plasma was isolated and applied to a glass slide-based Quantibody Mouse Cytokine Array (RayBiotech, Cat no: QAM-CAA-4000) according to the manufacturer's instruction, and the level of IL-1α (in pg/ml) was determined. Each mouse exhibited different level of increase in IL-1α concentration (FIG. 5C) and in average there was an increased level ~3 fold (p=0.002, FIG. 5A). FIG. 5B shows the fold-change for IL-1α obtained by calculating the ratio of treatment:reference/baseline IL-1α levels.

FIGS. 6A and 6B show tumor growth in individual mice (FIG. 6B) and in all groups (FIG. 6A). FIG. 6C shows that mice treated with radiotherapy in combination with anti-IL-1α or anti-IL-1β exhibited better survival rates than control mice or mice treated with radiotherapy alone.

DETAILED DESCRIPTION OF THE INVENTION

Before describing the methods of the invention, it should be understood that this invention is not limited to the particular methodology and protocols as described herein. It is also to be understood that the terminology used herein is for the purpose of describing particular embodiments of the invention only and, if not defined otherwise, it is not intended to limit the scope of the present invention which will be recited in the appended claims.

It must also be noted that as used herein and in the appended claims, the singular form "a", "an", and "the" include plural reference unless the context clearly dictates otherwise.

"Radiotherapy", used herein interchangeably with the term "radiation therapy", is a type of cancer treatment that uses beams of intense energy to kill cancer cells. Radiation therapy most often uses X-rays, but gamma rays, electron beams, or protons also can be used. The term "radiation therapy" most often refers to external beam radiation therapy. During this type of radiation, the high-energy beams come from a machine outside of the patient's body that aims the beams at a precise point on the body. Each session is quick and painless, lasting about 15 minutes.

As used herein, the term "session" or "session of treatment" refers to each radiotherapy treatment. A radiation therapy "regimen" or "schedule" usually consists of a specific number of treatments given over a set period of time, depending on the type and the stage of the cancer. Typically, for breast cancer, the patient has treatment sessions 5 times per week, Monday through Friday. This schedule may continue from 3 to 9, preferably 5 to 8, weeks. This schedule is referred herein after as "standard radiotherapy schedule".

The full dose of radiation is usually divided into a number of smaller doses called "fractions". For example, whole-breast radiation therapy after breast cancer surgery is usually given as one treatment per day, 5 days a week, for 5 to 7 weeks. The amount, "dose of radiation", used in radiotherapy is measured in gray (Cry), and varies depending on the type and stage of cancer being treated. In this 5-week treatment schedule of breast cancer, a total dose of 40 to 50 Cry is the usual amount given during the 5 weeks, in fractions of 2 Gray at each treatment.

A different radiation therapy schedule was developed that involves fewer treatments, e.g., twice a week, with higher doses of radiation at each treatment, but the same total radiation dose is given as in standard radiotherapy schedule. This "accelerated" or "hypofractionated" radiation schedule puts the same radiation total dose into two treatments a week in a 3 to 5-week schedule.

In one aspect, the present invention relates to a blocking agent to IL-1α, IL-1β or to their receptor IL-1R, selected from an anti-IL-1α, anti-IL-1β and anti-IL-1R, for use in the treatment of a cancer patient comprising administering said blocking agent to the patient in combination with radiotherapy, as described hereinbefore in the Summary of the Invention.

In another aspect, the present invention relates to treatment of a cancer patient that generates IL-1α or IL-1β, or both, in response to the treatment with radiotherapy (herein "host-induced IL-1α or IL-1β"), said method comprising administering to the patient an agent that blocks the activity of the host-induced IL-1α or IL-1β, or blocks the IL-1 receptor, in combination with radiotherapy, as described hereinbefore in the Summary of the Invention, to improve the therapeutic outcome of the treatment of the cancer patient with said radiotherapy.

The identification of the cancer patients which exhibit circulating host-induced IL-1a or IL-1β, or both, and can benefit from the treatment according to the present invention is based on the teaching of the above-mentioned International Patent Application No. PCT/IL2018/050608 (WO 2018/225062), in which the level of each factor generated by the patient in response to a cancer therapy treatment ("host response") is determined in a biological sample obtained from the cancer patient, preferably blood plasma, after a session of treatment with the cancer therapy. The value (factor concentration in pg/mL) obtained for each factor is then compared with a reference level, which is the baseline level of concentration of the same factor determined in a biological sample, preferably blood plasma, obtained previously from the same cancer patient (hereinafter "reference/baseline sample"). The change in the level of one or more of the factors identified in the biological sample obtained from the patient after the treatment compared to the reference/baseline sample, is defined by the fold change for each factor, determined by calculating the ratio of treatment: reference/baseline value for the factor. A fold change value of ≥1.5 (at least 1.5) indicates upregulation of the factor and is considered significant and predictive of a non-favorable response of the cancer patient to the treatment with the cancer therapy modality, while a fold change of ≤0.5 indicates down-regulation of the factor and is considered significant and predictive of a favorable response of the cancer patient to the treatment with the cancer therapy modality. For example, if the identified factor showing a fold-change of 1.5 or more is a pro-tumorigenic factor, it is predictive of the patient's non-favorable response to the treatment with the cancer therapy modality that induced the host-response.

Both IL-1α and IL-1β are tumorigenic factors and cancer patients that show an increase (up-regulation) of at least about 1.5 fold in their level after treatment with radiotherapy will not be responsive to the treatment with radiotherapy. In this case, the present invention proposes to administer to the patient an agent that blocks the tumorigenic activity of IL-1α and/or IL-1β, or an agent that blocks the IL-1 receptor to which both IL-1α and IL-1β bind to induce signaling, during the treatment with radiotherapy.

According to the invention, the biological samples of the cancer patient in which the assay is performed to determine the level of IL-1α, IL-1β or both, after a session of treatment with radiotherapy (i) and before the session of treatment (ii) may be selected from blood plasma, whole blood, blood serum or peripheral blood mononuclear cells. It is important that the biological samples (i) and (ii) are of the same type. In one preferred embodiment, the biological samples of step (i) and step (ii) are both blood plasma.

In one embodiment, the blocking agent of the invention blocks the activity of IL-1β or of its receptor IL-1R, and may be selected from: (a) an IL-1R antagonist (IL-1Ra); (b) a soluble decoy IL-1R receptor; (c) an anti-IL-1β neutralizing monoclonal antibody; (d) an anti-IL-1R neutralizing monoclonal antibody; (e) an IL-1β-converting enzyme (ICE) inhibitor; and (f) an IL-1β vaccine.

In one preferred embodiment, the active agent that blocks the protumorigenic activity of IL-1β or blocks its receptor IL-1R is Anakinra, a recombinant, nonglycosylated form of the human interleukin-1 receptor antagonist (IL-1Ra). Anakinra is produced by recombinant DNA technology using an *E. coli* expression system and differs from native human IL-1Ra by a single methionine residue added at its amino terminus.

In other embodiments, the active agent that blocks the protumorigenic activity of IL-1β or blocks its receptor IL-1R is an IL-1R antagonist selected from: (a) a pegylated 1L-1Ra such as VRS-826 (IL-1ra-rPEG), a chimeric IL-1Ra-IL-1β such as isunakinra (EBI-005), or a hybrid IL-1Ra molecule such as HL 2351 (rhIL-1Ra-hyFc). In further embodiments, the active agent that blocks the pro-tumorigenic activity of IL-1β is: (b) rilonacept, the soluble decoy IL-1 type I receptor; (c) the anti-IL-1β neutralizing monoclonal antibody is canakinumab, gevokizumab, LY2189102, or Lutikizumab (ABT-981); (d) the anti-IL-1R neutralizing antibody is MEDI-8968 or GSK1827771; (e) the IL-1β-converting enzyme inhibitor is Pralnacasan or Belnacasan; and (f) the IL-1β vaccine is hIL1bQb.

In another embodiment, the blocking agent of the invention blocks the activity of IL-1α or of its receptor IL-1R.

In one embodiment, the anti-IL-1α blocking agent according to the invention is an anti-IL-1α neutralizing monoclonal antibody (anti-hIL-1α-IgG). In other embodiments, the blocking agent blocks the activity of the receptor IL-1R and is as defined above. In preferred embodiments, also for blocking IL-1α activity the preferred blocking agent is Anakinra, As can be understood from the above, in patients that radiotherapy treatment induces IL-1α, IL-1β or both in the circulation of said cancer patient in response to treatment with the radiotherapy, the present invention proposes to determine the fold-change of each of the induced IL-1α, IL-1β or both by measuring the levels of the cytokines in biological samples obtained from the patient at certain time points before and after the radiotherapy treatment. This determination is preferably made when treatment is started, to decide whether to continue with the radiotherapy treatment, but may be made also in the middle of a radiotherapy schedule of treatment for monitoring the treatment. The time point may change according to the type of radiotherapy schedule: the standard or the hypofractionated schedule, as defined hereinbefore.

In one embodiment, the session of treatment with the radiotherapy is a first session of treatment in a course of therapy sessions with said radiotherapy, and the biological sample, preferably blood plasma, is obtained from the cancer patient at about 20 to 24 hours, after said first session of treatment with standard radiotherapy schedule, or at about 20 to 72 hours, including 24, 30, 36, 40, 48, 50, 60 hours or more, after said first session of treatment with accelerated/hypofractionated radiotherapy schedule, and said reference biological sample is obtained from said cancer patient at a time point of 72 hours or less, including at about 60, 50, 48, 40, 36, 30, 24 or 20 hours or less or just before said first session of treatment with the radiotherapy.

In another embodiment, the session of treatment with the radiotherapy is one of multiple sessions of treatment that is not the first session of treatment with the radiotherapy, and the biological sample, preferably blood plasma, is obtained from the cancer patient at about 20 to 24 hours, after said session of treatment that is not the first session of treatment with standard radiotherapy schedule, or at about 20 to 72 hours, including 24, 30, 36, 40, 48, 50, to 60 hours or more after said session of treatment that is not the first session of treatment with accelerated/hypofractionated radiotherapy schedule, and the reference/baseline biological sample is obtained from the cancer patient at a time point of 72 hours or less, including at about 20, 24, 30, 36, 40, 48, 50, 60, 72 hours or less or just before said session of treatment that preceded the session that is not the first session of treatment.

The combination of the blocking agent and the radiotherapy of the invention can be used for treating cancer patients shown to generate IL-1α, IL-1β or both in response to treatment with radiotherapy alone, and suffering from a primary or a metastatic cancer including bladder, breast, brain, cervical, colon, colorectal, head and neck, kidney, lung, melanoma, ovarian, pancreas, prostate, skin, thyroid and uterine cancer, leukemia, lymphoma, multiple myeloma and sarcoma.

In one embodiment, for treatment of breast cancer, anakinra is administered daily either in a standard radiotherapy treatment schedule of 5 sessions a week, during 5 to 9, preferably 5-8, weeks, or in an accelerated/hypofractionated radiotherapy treatment schedule of 2 sessions per week, during of 3-4 weeks, wherein the same total radiation dose is administered in both radiotherapy schedules. In this treatment, anakinra may be administered to the cancer patient either before or after the radiotherapy session.

In another embodiment, the blocking agent is an anti-IL-1β neutralizing monoclonal antibody or an anti-IL-1α neutralizing monoclonal antibody, that may be administered once every 2-3 weeks either in a standard radiotherapy treatment schedule of 5 sessions a week, during 5 to 9, preferably 5-8, weeks, or in an accelerated/hypofractionated radiotherapy treatment schedule of 2 sessions a week, during 3 to 4 weeks, wherein the same total radiation dose is administered in both radiotherapy schedules.

Figure 4A:
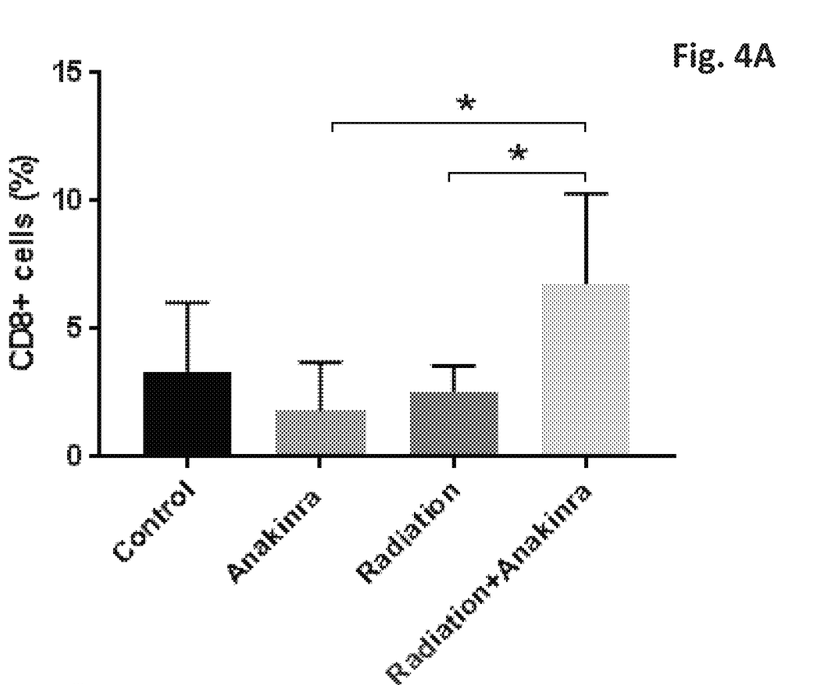
Figure 4B:
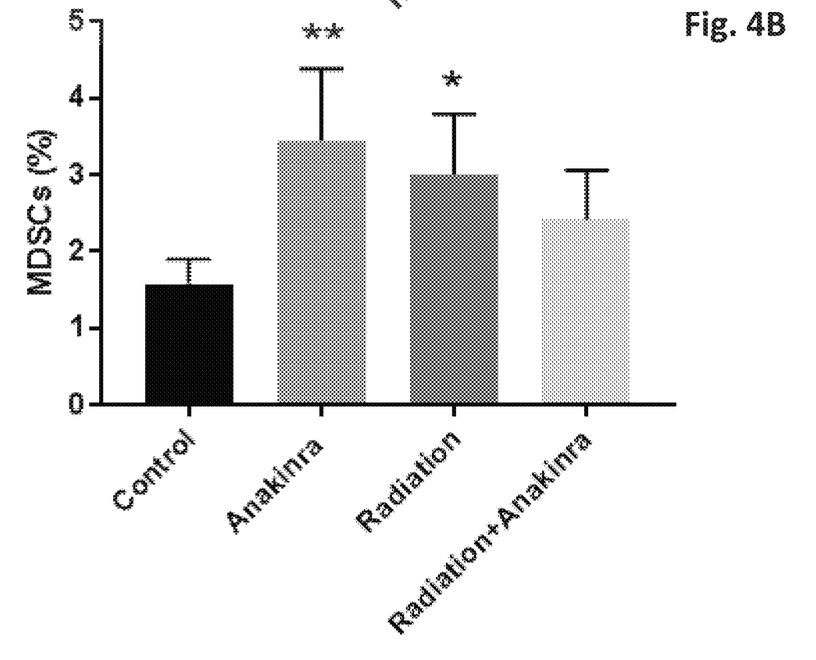

As shown in the examples and in the figures of the present application, treatment with radiotherapy in combination with the blocking agent to IL-1α, IL-1β or anti-IL-1R has greater anti-tumor and pro-survival effects. It is also shown (Example 3, FIG. 4) that combination of radiotherapy with anakinra reveals an increase in CD8+ cytotoxic Tcells, suggesting that inhibition of tumor growth following radiotherapy and anakinra is mediated, at least in part, by CD8+T cytotoxic cells. Moreover, while mice treated with radiotherapy or anakinra exhibited a significant increase in tumor-infiltrating myeloid-derived suppressor cells (MDSCs) compared to control mice, the combined treatment of radiotherapy and anakinra has led to decreased levels of MDSCs. These results suggest, without excluding a role for other cell types, that the inhibition of tumor growth in the combined treatment of radiotherapy and anakinra is mediated, at least in part, by reducing MDSCs and inducing CD8+T infiltrating cells compared to each treatment alone.

Thus, in a further embodiment, the present invention relates to treatment of a cancer patient with the combination of radiotherapy and a blocking agent to IL-1α, IL-1β or anti-IL-1R, preferably anakinra, wherein the inhibition of tumor growth is due to anti-tumor immunity resulting in increased number of CD8+T cytotoxic cells and decreased number of myeloid-derived suppressor cells (MDSCs).

The invention will now be illustrated by the following non-limiting Examples.

EXAMPLES

Materials and Methods
(i) Materials:
Anakinra—Kineret 100 mg, Sobi, cat #an-0347 Lot: 31301-1F; InVivoMAb anti-mouse/rat IL-1β Clone B122, Bio X Cell, Catalog #BE0246, Lot: 676418A1; InVivoMAb anti-mouse IL-1α Clone ALF-161, Bio X Cell, Catalog #BE0243, Lot: 63471J1; InVivoMAb anti-mouse IL-1R (CD121a) Clone JAMA-147, Bio X Cell, Catalog #BE0256, Lot: 654617J3.

(ii) Tumor Cell Cultures:
Murine EMT6 breast carcinoma and CT26 murine colon carcinoma cell lines were purchased from the American Type Culture Collection (ATCC, USA). The cells were passaged in culture for no more than 4 months after being thawed from authentic stocks. Cultures were tested to be negative for *mycoplasma*. EMT6 and CT26 cells were cultured in Dulbecco's modified eagle medium (DMEM) and RPMI Media 1640 medium, respectively, each medium supplemented with 10% fetal bovine serum (FBS), 1% L-glutamine, 1% sodium-pyruvate and 1% penicillin-streptomycin (Biological Industries, Israel) at 37° C. in 5% $CO_2$.

(iii) Animals, Treatment Protocols and Tumor Models:

Naïve 8-10 weeks old female BALB/c mice were used in this study (Harlan, Israel). EMT6 murine breast carcinoma cells ($5 \times 10^5$) were implanted in BALB/c mice into the mammary fat pad. Tumor size was assessed regularly with Vernier calipers using the formula $width^2 \times length \times 0.5$. When tumors reached a size of 150-250 $mm^3$, different treatments were initiated. Mice were locally irradiated to the abdominal cavity with a linear accelerator 6 MeV electron beam using Elekta Precise (Elekta Oncology Systems) at a dose rate of 40 cGy per minute, for a total dose of 2 Gy at room temperature. Anakinra (Swedish Orphan Biovitrum) was injected intraperitoneally at a dose of 10 mg/kg daily for 4 consecutive days, starting 1 day before radiation. Control mice were injected with vehicle control. Tumor size was assessed twice a week using a calibrator. The experiment was terminated when tumors reached a size of ~1000 $mm^3$, at which point mice were sacrificed, and lungs and tumors were removed for further analysis.

(iv) IL-1α Quantification by Protein Array:

Plasma was isolated and applied to a glass slide-based Quantibody Mouse Cytokine Array (RayBiotech, Cat no: QAM-CAA-4000) according to the manufacturer's instruction, and the level of IL-1α in the plasma (in pg/ml) was determined.

(v) IL-1β Quantification by ELISA:

Spleens (extracted from control or irradiated mice) were homogenized in PBS containing 20 mmol/L HEPES, 100 mmol/L NaCl, 1 mmol/L EDTA, 1% Triton, and a protease inhibitor mixture (Roche Diagnostics). The homogenates were centrifuged and supernatants collected. Equal amounts of protein were applied to a mouse IL-1β ELISA kit (R&D Systems, Inc.) in accordance with the manufacturer's instructions.

(vi) Flow Cytometry:

To analyze tumor-infiltrating immune cells, tumors were prepared as a single cell suspension and cells were immunostained for the following antibodies against specific surface markers which discriminate between the various cell populations as follows: MDSCs—CD11b+/Gr-1+/Ly6G+/Ly6C+; M1 macrophages—CD45+/CD11c+/CD206−/F4/80+; M2 macrophages—CD45+/CD11c−/CD206+/F4/80+; cytotoxic T lymphocytes (CD8+/CD25+), T helper cells (CD4+), and T regulatory cells (CD4+/CD25+/FOXp3+). All monoclonal antibodies were purchased from Bio Legend, BD Biosciences, or R&D systems and used in accordance with the manufacturers' instructions. At least 100,000 events were acquired using a Cyan ADP flow cytometer and analyzed with Summit v4.3 software (Beckman Coulter).

(vii) Statistical Analysis:

Data is expressed as mean±standard deviation (SD). For the IL-1β quantification by ELISA, the statistical significance of differences was assessed by two tailed unpaired t test. For the tumor growth assessment, the statistical significance of differences was assessed by one-way ANOVA. Differences between all groups were compared with each other and were considered significant at p values below 0.05.

Example 1. Induction of Host-Derived IL-1β Expression Following Radiotherapy

Figure 1A:
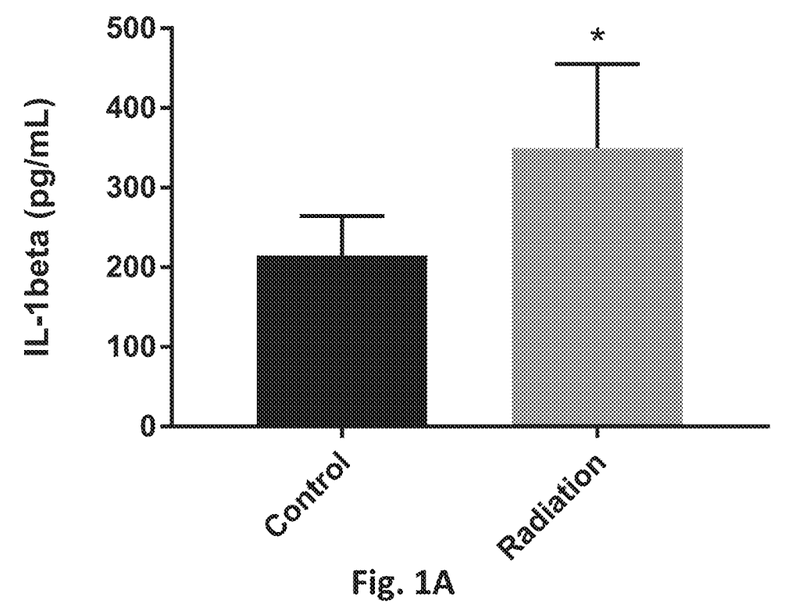
FIGS. 1A-1B show the effect of radiation on IL-1β levels in non-tumor bearing BALB/c mice compared to baseline. Naïve BALB/c mice (8-10 weeks old) were exposed to a single dose of 2Gy radiation in the abdominal region. Control mice were not irradiated. After 24 hours, the mice were sacrificed and the level of IL-1β in spleen lysates (FIG. 1A) was determined by ELISA. Shown are mean values (n=7 mice per group)±SD, *p<0.05.
Figure 1B:
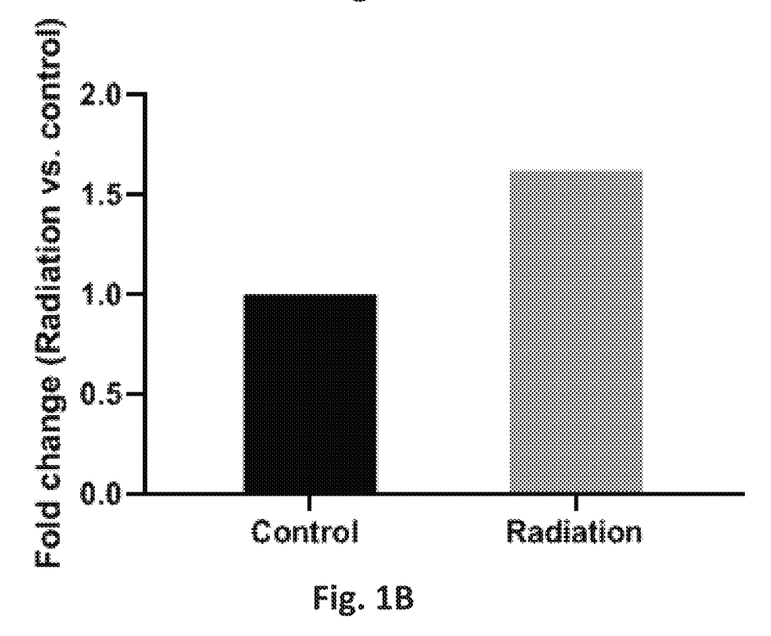

To identify whether host-derived IL-1β expression is unregulated in response to radiotherapy, naïve (non-tumor bearing) BALB/c mice (8-10 weeks old) were exposed to a single dose of 2Gy radiation in the abdominal region. After 24 hours, the mice were sacrificed and the level of IL-1β in spleen lysates was determined by ELISA. Control mice were not irradiated. FIG. 1A shows a significant increase in the level of IL-1β in irradiated mice compared to control, and FIG. 1B shows a fold-change of at least 1.5 as calculated by the ratio of measured levels of IL-1β in the spleen lysates of control vs. treated mice. Of note, since this experiment was performed using naïve mice, it demonstrates that IL-1β is produced by host cells in response to radiation, independent of tumor presence. Shown are mean values (n=7 mice per group)±SD, *p<0.05.

Example 2. Blocking of Radiotherapy-Induced Host-Derived IL-1β Inhibits Primary Tumor Growth and Improves Mice Survival In principle, agents that antagonize pro-tumorigenic factors upregulated in response to anti-cancer therapies could be used as complementary therapies to improve treatment outcome. Here the therapeutic potential of counteracting IL-1β upregulation induced in response to radiation was investigated.

Figure 2A:
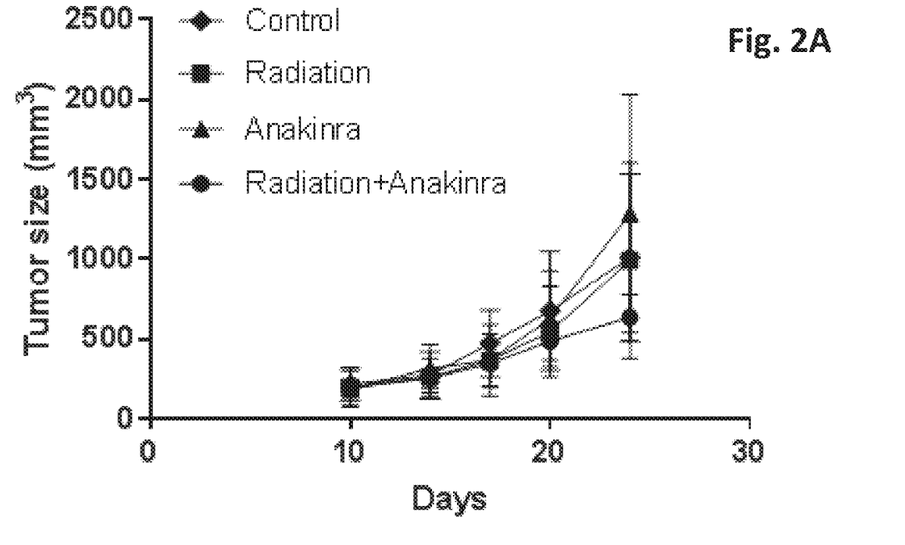
Figure 2B:
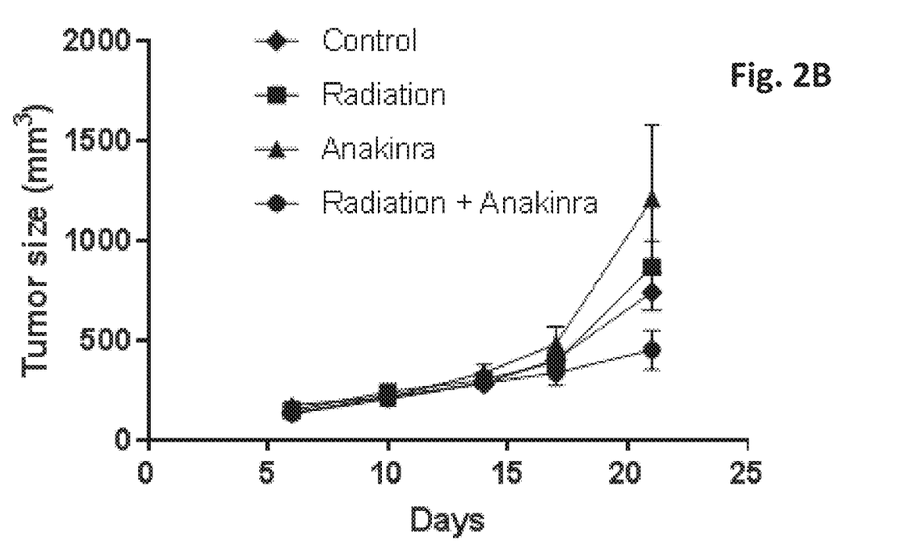

To study whether blocking host-derived IL-1β (which is upregulated in response to radiation) improves the efficacy of radiotherapy, BALB/c mice were orthotopically injected with EMT6 murine breast carcinoma cells into the mammary fat pad. When tumors reached a size of 150-250 $mm^3$, mice were either exposed to a single dose of 2Gy radiation (2A) or to a total of four doses (single dose of 2Gy twice a week, FIG. 2B) in the abdominal region, treated with anakinra alone for 4 sequential days, starting one day before the radiation, or treated with a combination of radiation and anakinra. Control mice were injected with vehicle control. Tumor growth was monitored regularly. The results in FIG. 2A show that the combined treatment of radiation and anakinra inhibits primary tumor growth compared to the other groups. FIG. 2B shows a similar experiment in which the animals were exposed twice a week to radiation and demonstrates enhanced anti-tumor effect of the combined radiation and anakinra treatment group over the control, radiation-alone and anakinra-alone treated mice (p values 0.053, 0.025 and 0.058, respectively). Together, these results demonstrate that blocking host-derived IL-1β in combination with radiotherapy inhibits primary tumor growth especially in a long-term repeated treatment. Control mice were injected with vehicle control. Tumor volume was monitored regularly. Shown are mean values (n=6 mice per group)±SD.

Figure 3:
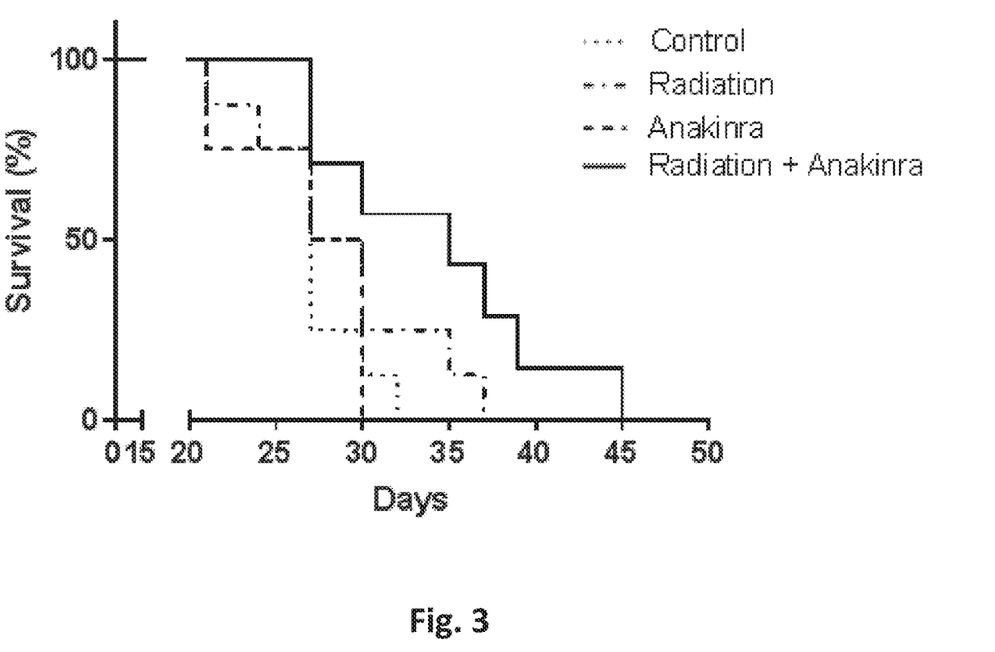
FIG. 3 is a Kaplan-Meir curve showing the survival rate of the mice described in FIG. 2B following treatment with radiation, anakinra or radiation along with anakinra. Control mice were treated with vehicle alone. Shown are mean values (n=7 mice per group).

Blocking host-derived IL-1β in combination with radiotherapy did not only improve tumor burden but also improved mice survival. As shown in FIG. 3, mice treated with radiotherapy in combination with anakinra exhibited enhanced survival rate (median survival of 35 days) compared to mice treated with anakinra, radiation or vehicle control alone (median survival of 28.5, 28.5 and 27, respectively), p value=0.03, 0.09 and 0.01, respectively.

Example 3. Blocking Radiotherapy-Induced Host-Derived IL-1β Affects the Number of Tumor-Infiltrating Immune Cells BALB/c mice were orthotopically injected with EMT6 murine breast carcinoma cells in the mammary fat pad. When tumors reached a size of 150-250 $mm^3$, mice (4 experimental groups) were either exposed to a single dose of local 2Gy radiation, treated with anakinra for 4 sequential days starting two days before the radiation, treated with a combination of radiation and anakinra, and control mice were injected with vehicle control. At the end of the experiment (when tumors reached a size of ~1000 mm$^3$), mice were sacrificed, tumors were removed and prepared as a single cell suspension. Cells were immunostained for biomarkers characterizing different immune cells populations to understand the mechanism by which the tested cancer therapy helps to inhibit tumor growth, and flow cytometry analysis of the tumor-infiltrating immune cells was performed. The analysis revealed an increase in CD8+ cytotoxic T cells (see FIG. 4A, p<0.05), suggesting that inhibition of tumor growth following radiotherapy and anakinra is mediated, at least in part, by CD8+T cytotoxic cells. Moreover, while mice treated with radiotherapy or anakinra exhibited a significant increase in tumor-infiltrating myeloid-derived suppressor cells (MDSCs) compared to control mice, the combined treatment of radiotherapy and anakinra has led to decreased levels of MDSCs, which reached their level in the control mice (see FIG. 4B, * p<0.0.5, ** p<0.01). MDSCs suppress the immune response and have been shown to infiltrate many tumor types. These results suggest, without excluding a role for other cell types, that the inhibition of tumor growth in the combined treatment of radiotherapy and anakinra is mediated, at least in part, by reducing MDSCs and inducing CD8+T infiltrating cells compared to each treatment alone.

Example 4. Induction of Host-Derived IL-1α Expression Following Radiotherapy

To determine whether not only host-derived IL-1β but also host-derived IL-1α is upregulated in response to radiotherapy, a protein array was performed on plasma samples from naïve mice exposed to radiation.

Figure 5A:
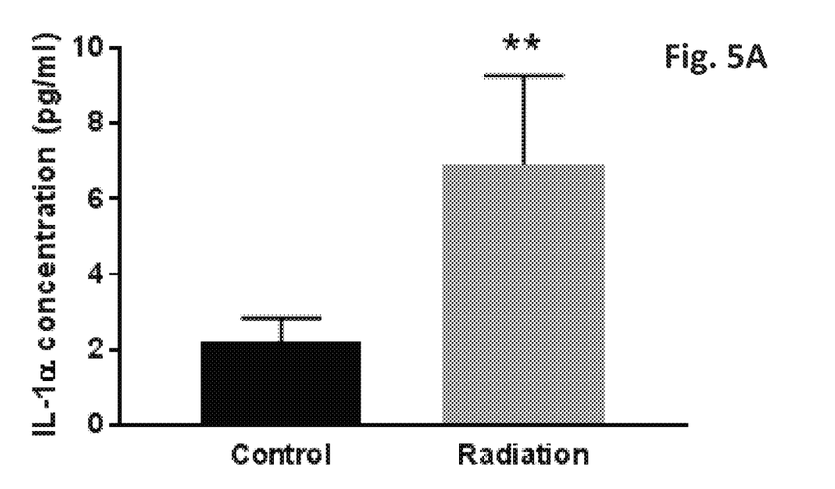
Figure 5B:
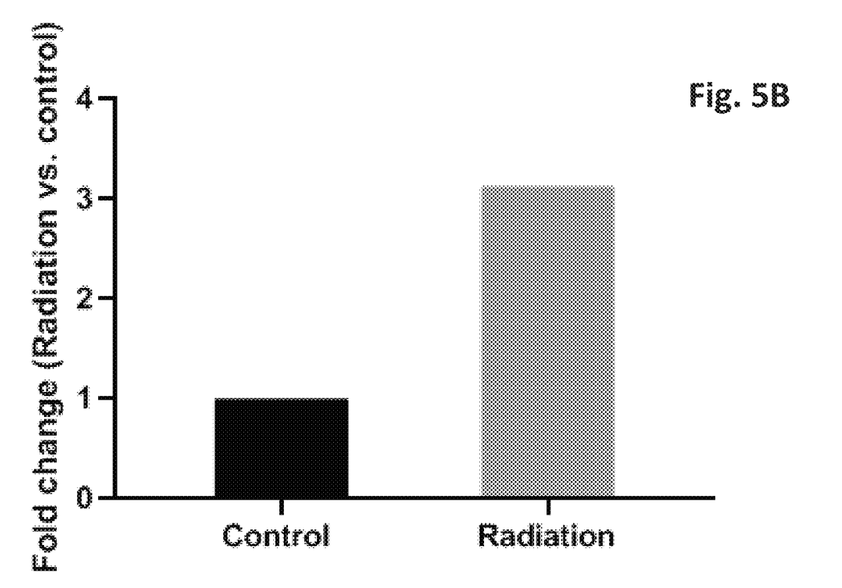
Figure 5C:
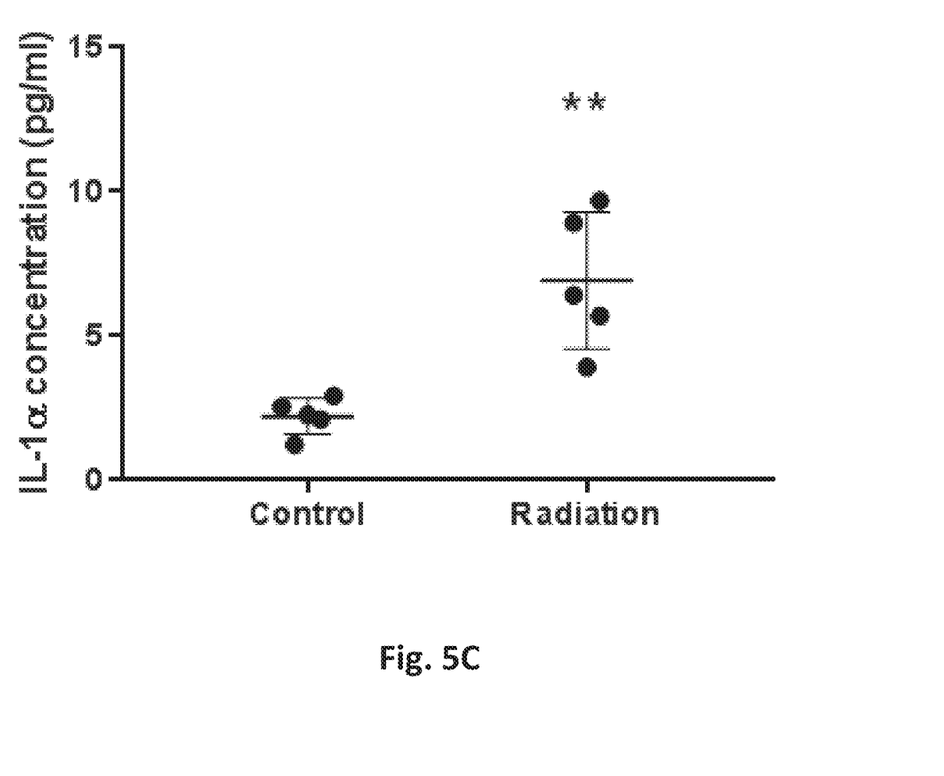

Six weeks old naïve female BALB/c mice (n=5) were exposed to a single dose of 2Gy radiation in the abdominal cavity (treatment group) or were not treated (control group). After 24 hours, mice were sacrificed, and blood was collected into EDTA-coated tubes by cardiac puncture. Plasma was isolated and applied to a glass slide-based Quantibody Mouse Cytokine Array (RayBiotech, Cat no: QAM-CAA-4000) according to the manufacturer's instruction, and the level of IL-1α (in pg/ml) was determined. FIGS. 5A and 5C show the increase in IL-1α concentration in response to radiotherapy, and FIG. 5B shows the calculated fold-change thereof. As demonstrated, each mouse showed different level of increase of the IL-1α concentration (FIG. 5C) and in average there was an increased ~3 fold (p=0.002, FIG. 5A) in mice treated with radiation compared to control mice (The fold change was determined by calculating the ratio of treated:control values. A fold change of more than 1.5 was defined as being upregulated in response to radiotherapy). Of note, since this experiment was performed using naïve mice, it demonstrates that IL-1α is produced by host cells in response to radiation, independent of tumor presence.

Figure 6A:
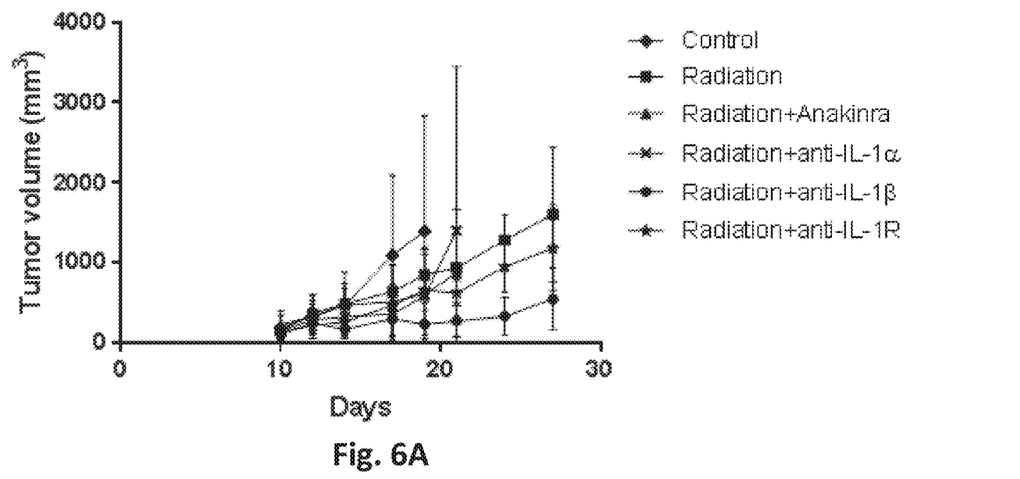
FIGS. 6A-6C show that blocking IL-1α, IL-1β or IL-1R in combination with radiation has greater anti-tumor and pro-survival effects than radiation alone in a mouse model of colon cancer. 2×10⁶ CT26 colon tumor cells were subcutaneously implanted into the right flank of BALB/c female mice to form tumors. When tumor reached a size of 100 mm³, mice were treated with radiation alone (total dose of 2Gy, twice a week) or in combination with 10 mg/kg hIL-1RA (Anakinra, daily IP injected), neutralizing antibody against IL-1α (anti-IL-1α, 200 μg twice a week), neutralizing antibody against IL-1β (anti-IL-1β, 200 μg twice a week), or neutralizing antibody against mIL-1R (anti-mIL-1R, 580 μg twice a week). Control mice were left untreated. Tumors' growth was monitored regularly, and when tumors reached a size of ~1500 mm³, mice were sacrificed.
Figure 6B:
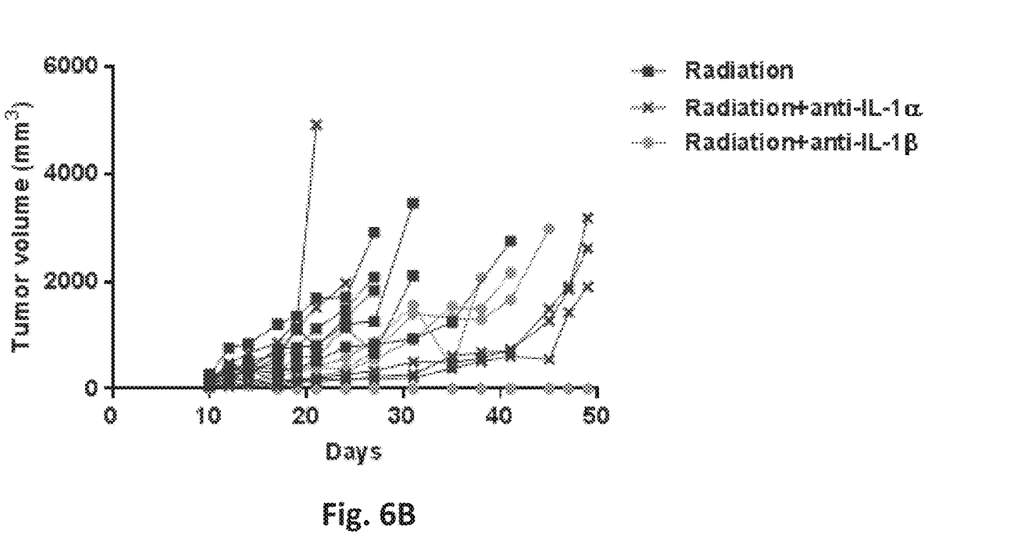
Figure 6C:
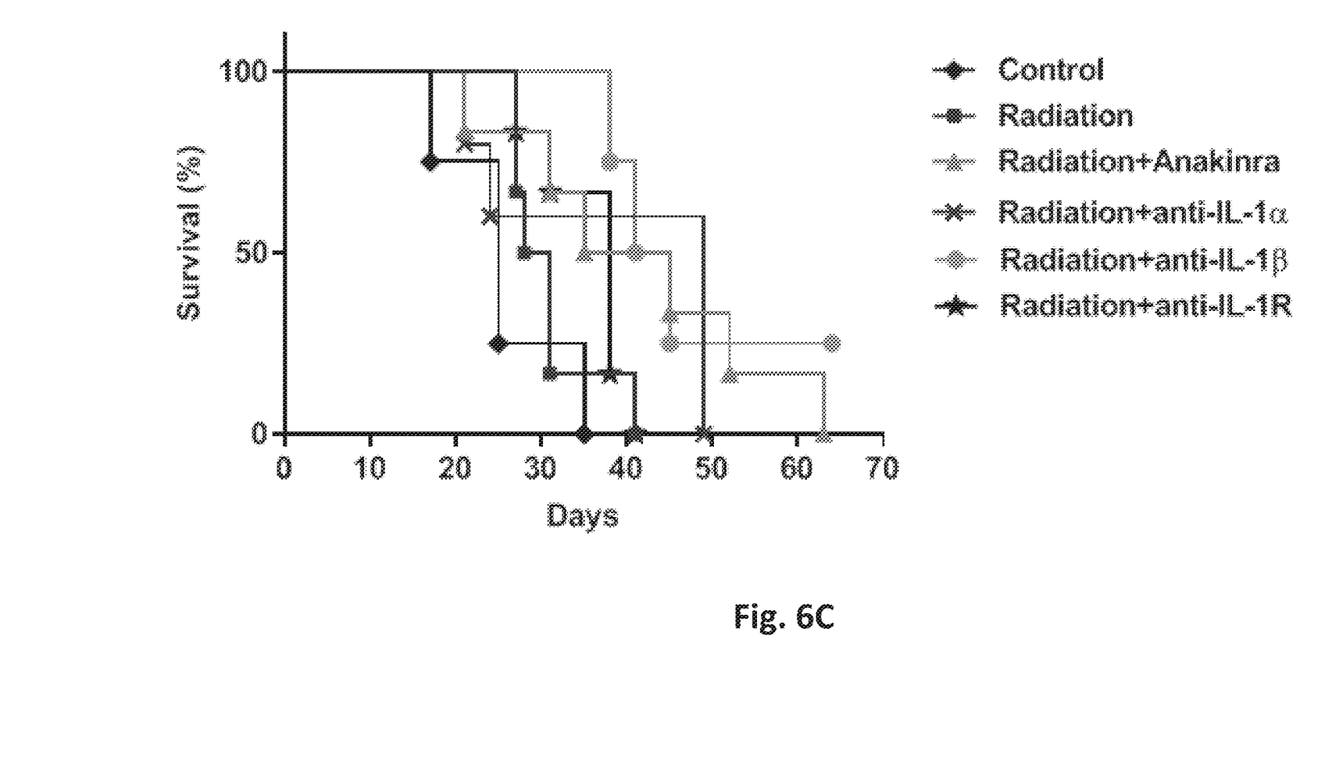

Example 5. Blocking IL-1α, IL-1β or IL-1R in Combination with Radiation has a Greater Anti-Tumor Effect than Radiation Alone in a Mouse Model of Colon Cancer Since both IL-1α and IL-1β share the same receptor, IL-1R, tumor growth inhibition by blocking each one of them in combination with radiation therapy was then tested in order to dissect the pro-tumorigenic role of each one of the ligands. For this purpose, 2×10$^6$ CT26 colon tumor cells were subcutaneously implanted into the right flank of BALB/c female mice to form tumors. When tumor reached a size of 100 mm$^3$, mice were treated with radiation alone (total dose of 2Gy, twice a week) or in combination with 10 mg/kg hIL-1RA (Anakinra, daily IP injected), neutralizing antibody against IL-1α (anti-IL-1α, 200 µg twice a week), neutralizing antibody against IL-1β (anti-IL-1β, 200 µg twice a week), or neutralizing antibody against mIL-1R (anti-mIL-1R, 580 µg twice a week). Control mice were left untreated. Tumors' growth was monitored regularly and, when tumors reached a size of 1500 mm$^3$, mice were sacrificed. Of note, when one mouse of a certain treatment group was sacrificed, no further measurements of this certain group were taken into consideration. As shown in FIG. 6A, while control mice reached a maximum tumor volume already at day 19, all other group treatments showed reduced tumor growth. Moreover, treatments of radiation in combination with anti-IL-1α, anti-IL-1β or anti-mIL-1R were found to be more effective in inhibiting tumor growth compared to radiation alone. The advantage of the combined treatment compared to radiation alone in inhibiting tumor growth is more emphasized when comparing tumor growth in single mice, as demonstrated in FIG. 6B. In addition, when calculating the survival of the mice until they reached endpoint (FIG. 6 C), mice treated with radiation in combination with anti-IL-1α or anti-IL-1β exhibited better survival rates than control mice or mice treated with radiotherapy alone. Overall, these results show that treatments combining radiation with IL-1α, IL-1β or IL-1R inhibitors (and probably also combination thereof) exhibit improved anti-tumor activity and confer better survival compared to control or radiation alone.

REFERENCES

Apte, R N, Dotan S, . . . , Voronov E. The involvement of IL-1 in tumorigenesis, tumor invasiveness, metastasis and tumor-host interactions. Cancer Metastasis Rev, 2006; 25(3): p. 387-408

Beyar-Katz O, . . . , Shaked Y. Bortezomib-induced proinflammatory macrophages as a potential factor limiting anti-tumour efficacy. J Pathol. 2016; 239: p. 262-273

Dinarello, C. Why not treat human cancer with interleukin-1 blockade? Cancer Metastasis Review. 2010; 29: p. 317-329

Gingis-Velitski S, Loven D, Benayoun L, Munster M, Bril R, Voloshin T, Alishekevitz D, Bertolini F, Shaked Y. Host response to short-term, single-agent chemotherapy induces matrix metalloproteinase-9 expression and accelerates metastasis in mice. Cancer Res. 2011; 71(22): p. 6986-96

Rachman-Tzemah, C., . . . , and Yuval Shaked. Blocking Surgically Induced Lysyl Oxidase Activity Reduces the Risk of Lung Metastases. Cell Rep, 2017. 19(4): p. 774-784

Shaked, Y., Balancing efficacy of and host immune responses to cancer therapy: the yin and yang effects. Nat Rev Clin Oncol, 2016. 13(10): p. 611-26

Timaner, M, . . . , and Yuval Shaked. Dequalinium blocks macrophage-induced metastasis following local radiation. Oncotarget, 2015. 6(29): p. 27537-54

Voronov, E., Shouval D S, . . . , and Ron N. Apte. IL-1 is required for tumor invasiveness and angiogenesis. Proc Natl Acad Sci USA, 2003. 100(5): p. 2645-50

The invention claimed is:

1. A method of treating a solid cancer in a subject in need thereof, the method comprising:

a. measuring IL-1α, IL-1β or both in a biological sample obtained from said subject at a time of 20 hours or more after a session of treatment with radiotherapy, wherein said radiotherapy is external beam radiotherapy, to determine the level of circulating IL-1α, IL-1β or both in response to radiotherapy in said subject, wherein said biological sample is selected from blood plasma, whole blood, blood serum or peripheral blood mononuclear cells;
b. obtaining a reference level for said circulating IL-1α, IL-1β or both in said subject before said session of treatment with said radiotherapy;
c. establishing a fold-change in said circulating IL-1α, IL-1β or both from said reference level to said level in response to radiotherapy;
d. determining said subject has a non-favorable response to said treatment with said radiotherapy if said fold-change is an increase of at least 1.5-fold; and
e. treating said subject determined to have a non-favorable response with said radiotherapy in combination with anakinra;

thereby treating a solid cancer in a subject in need thereof.

2. The method of claim 1, wherein said obtaining in step (b) is obtaining in a biological sample from said subject before said session of treatment with said radiotherapy, wherein said biological sample is selected from blood plasma, whole blood, blood serum or peripheral blood mononuclear cells.

3. The method of claim 1, wherein said biological sample of step (a) is blood plasma.

4. The method of claim 3, wherein said obtaining in step (b) is obtaining in blood plasma from said subject before said session of treatment with said radiotherapy.

5. The method of claim 1, wherein said treating is administering anakinra.

6. The method of claim 1, wherein said treating comprises inhibiting tumor growth, increasing the number of CD8+T cytotoxic cells and decreasing the number of myeloid-derived suppressor cells (MDSCs), or a combination thereof.

7. The method of claim 1, wherein said biological sample is obtained from the subject at 20 to 24 hours after a session of treatment with standard radiotherapy schedule, or 20 to 72 hours after a session of treatment with accelerated/hypofractionated radiotherapy.

8. The method of claim 1, wherein said session of treatment with radiotherapy is the first session of treatment with said radiotherapy.

9. The method of claim 1, wherein said reference level is obtained in a reference biological sample obtained from said subject at most 72 hours before said treatment with said radiotherapy.

10. The method of claim 9, wherein said session of treatment with radiotherapy is not the first session of treatment with said radiotherapy, and wherein said reference level is obtained at least 72 hours after an earlier session of treatment with said radiotherapy, wherein said earlier session of treatment with said radiotherapy is a session of treatment before said not a first session of treatment with said radiotherapy.

11. The method of claim 1, wherein said session of treatment with radiotherapy is not the first session of treatment with said radiotherapy, and wherein said reference level is obtained at least 72 hours after an earlier session of treatment with said radiotherapy, wherein said earlier session of treatment with said radiotherapy is a session of treatment before said not a first session of treatment with said radiotherapy.

12. The method of claim 1, wherein said solid cancer is a primary or a metastatic solid cancer selected from bladder cancer, breast cancer, brain cancer, cervical cancer, colon cancer, colorectal cancer, head and neck cancer, kidney cancer, lung cancer, melanoma, ovarian cancer, pancreatic cancer, prostate cancer, skin cancer, thyroid cancer, uterine cancer and sarcoma.

13. The method of claim 1, wherein said treating comprises administering anakinra daily in a standard radiotherapy treatment schedule comprising 5 radiotherapy treatments a week for 5 to 9 weeks, or in an accelerated/hypofractionated radiotherapy treatment schedule comprising 2 radiotherapy treatments a week for 3 to 4 weeks and wherein the same total radiation dose is administered in both radiotherapy schedules.

14. The method of claim 1, wherein anakinra is administered before, after or with each radiotherapy session.

15. The method of claim 12, wherein said solid cancer is selected from breast cancer, and colon cancer.

16. The method of claim 1, wherein said external beam therapy is x-ray radiotherapy.

17. The method of claim 1, wherein said method is a method of converting a subject with a non-favorable response to radiotherapy to a subject with a favorable response.

18. The method of claim 1, wherein said method is a method of stimulating an anticancer immune response.

19. The method of claim 1, wherein said solid cancer is a cancer treatable by said radiotherapy.

* * * * *